United States Patent [19]

Naficy

[11] 4,298,998
[45] Nov. 10, 1981

[54] BREAST PROSTHESIS WITH BIOLOGICALLY ABSORBABLE OUTER CONTAINER

[76] Inventor: Sadeque S. Naficy, 9343 N. Loop East, Houston, Tex. 77029

[21] Appl. No.: 214,449

[22] Filed: Dec. 8, 1980

[51] Int. Cl.³ .............................................. A61F 1/24
[52] U.S. Cl. ........................................................ 3/36
[58] Field of Search ............................................. 3/36

[56] References Cited

U.S. PATENT DOCUMENTS

| | | | |
|---|---|---|---|
| 2,842,775 | 7/1958 | Pangman | 3/36 |
| 3,189,921 | 6/1965 | Pangman | 3/36 |
| 3,293,663 | 12/1966 | Cronin | 3/36 |
| 3,366,975 | 2/1968 | Pangman | 3/36 |
| 3,559,214 | 2/1971 | Pangman | 3/36 |
| 3,600,718 | 8/1971 | Boone | 3/36 |
| 3,663,968 | 5/1972 | Mohl et al. | 3/36 |
| 3,665,520 | 5/1972 | Perras et al. | 3/36 |
| 3,681,787 | 8/1972 | Perras | 3/36 |
| 3,683,424 | 8/1972 | Pangman | 3/36 |
| 3,852,832 | 12/1974 | McGhan et al. | 3/36 |
| 3,852,833 | 12/1974 | Koneke et al. | 3/36 |
| 3,919,724 | 11/1975 | Sanders et al. | 3/36 |
| 3,934,274 | 1/1976 | Hartley, Jr. | 3/36 |
| 3,986,213 | 10/1976 | Lynch | 3/36 |
| 4,035,850 | 7/1977 | Cresswall | 3/36 |

OTHER PUBLICATIONS

*Reconstructive Plastic Surgery*, Converse, 1980, (textbook) pp. 3694–3704.
"Plastic and Reconstructive Surgery" Dec. 1976, pp. 689–693; Aug. 1972, pp. 107–113; Nov. 1976, pp. 555–560; Aug. 1976, pp. 137–141; Jan. 1980, pp. 30–33; Nov. 1977, pp. 720–724; Aug. 1979, pp. 151–155; Jul. 1980, pp. 71–73; Jun. 1977, pp. 849–850; Mar. 1980, pp. 302–306.
"Aesthetic Plastic Surgery", 1978, 2:435–441, 2:217–234; 1979, 3:339–341.

*Primary Examiner*—Clifford D. Crowder
*Attorney, Agent, or Firm*—Neal J. Mosely

[57] ABSTRACT

A newly developed breast prosthesis overcomes the tightness and contracture of the fibrous capsule which forms around the existing prosthesis. The unique construction of the new prosthesis causes the capsule to form at a predetermined, controlled distance from the surface thereof. This prosthesis is constructed with a first phase or outer temporary component and a second phase or inner permanent component. The inner component is a container or sac of a flexible, non-absorbable material filled with a fluid or gel filler material. The temporary outer component is an outer container or cover of a material which is absorbable under the conditions of use, and an inert filler material, preferably an absorbable, biologically acceptable liquid, e.g. saline solution, filling the space between the inner and outer components. The inner component is preferably of silicone rubber film and is filled with a silicone gel. The outer portion is in the form of a sheet, film or coating of a material which can be absorbed in the body after surgical implantation. Suitable materials are ones which will be absorbed by phagocytosis or hydrolysis or other processes or which can be rendered absorbable by physical or chemical or enzymatic treatment or the like, prior to, during, or after surgical implantation. These materials include natural, synthetic or semisynthetic materials proven useful for surgical sutures and materials such as reconstituted collagen, polylactic acid, polyglycolic acid, polyglactin 910, reconstituted vegetable protein, etc.

26 Claims, 14 Drawing Figures

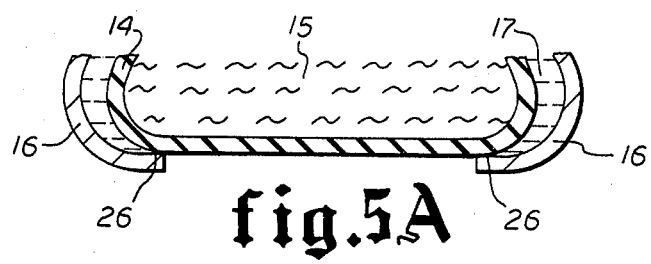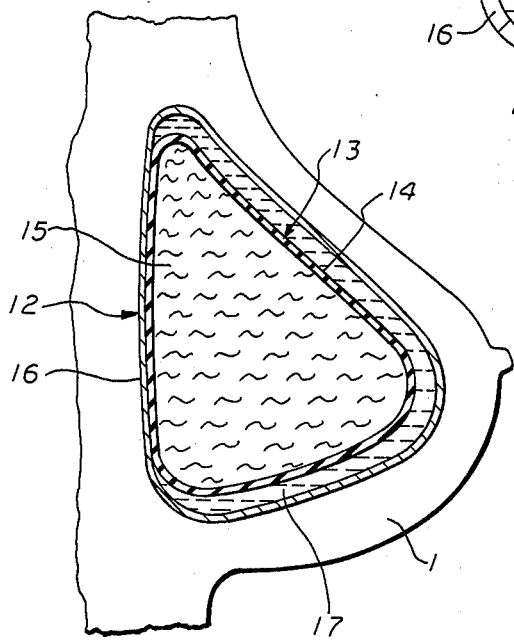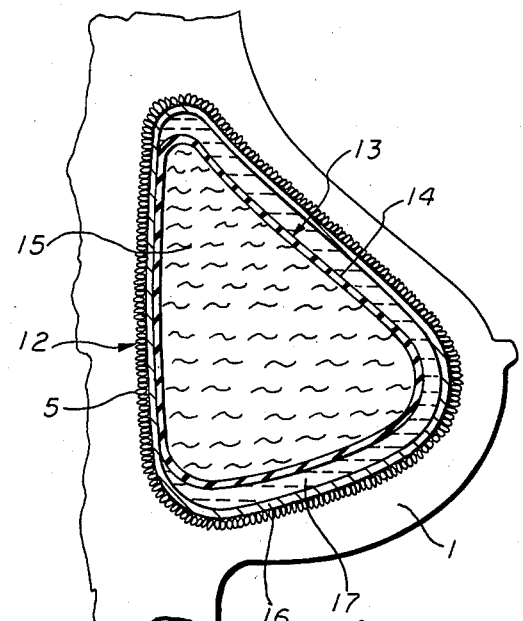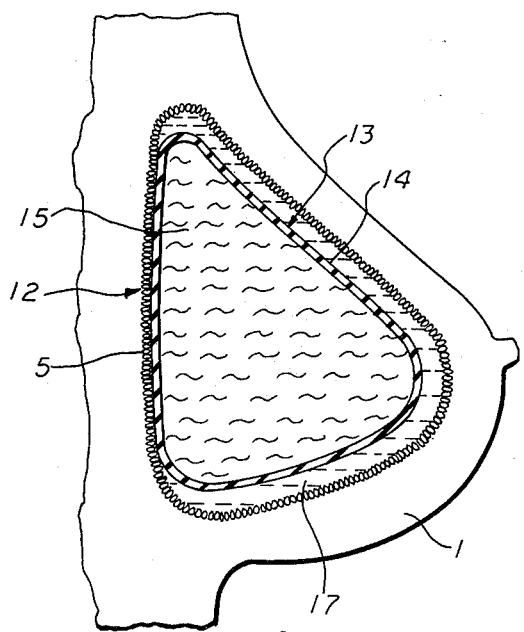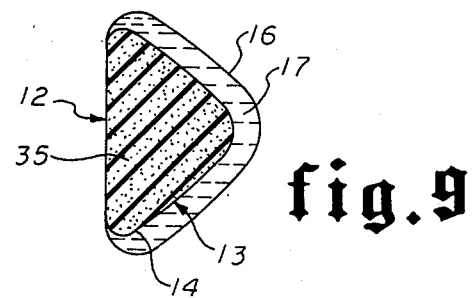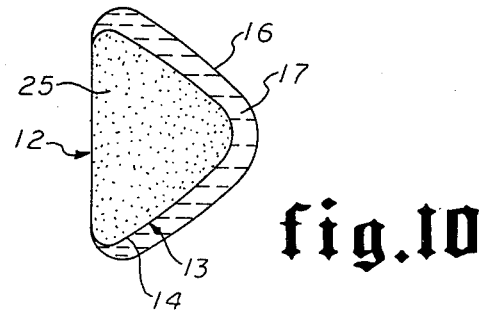

BREAST PROSTHESIS WITH BIOLOGICALLY ABSORBABLE OUTER CONTAINER

BACKGROUND OF THE INVENTION

1. Field of the Invention

This invention relates to new and useful improvements in a breast prosthesis suitable for implantation in a human breast for reconstructive or cosmetic purposes.

2. Brief Description of the Prior Art

Surgical reconstruction of human breasts as a result of injury or as a result of partial or total mastectomy has been performed for many years. In recent years, surgical augmentation of breasts has particularly become common for cosmetic purposes in cases of breast hypoplasia. Over the past 10–15 years, various surgical prostheses have been developed for implantation in the human breast as a part of breast reconstruction or augmentation. Recently developed prostheses have been satisfactory in some cases but in a substantial number of other cases significant degrees of capsular tightness or contracture has developed causing undesirable appearance associated with some pain and discomfort.

Surgical procedures for breast reconstruction are described in detail in the medical literature, particularly in Journals dealing with plastic surgery. Some of this literature describes prosthetic devices which are in common use. The recently published textbook RECONSTRUCTIVE PLASTIC SURGERY, CONVERSE, 1980, pp. 3694–3704 gives a thorough review of the history of the development of breast prostheses and of the problems involved. PLASTIC SURGERY, WILLIAM C. GRABB AND JAMES W. SMITH, 1979 is another text giving a thorough treatment of this subject. Representative medical journal references, listed somewhat in order of relevance and importance, are: PLASTIC AND RECONSTRUCTIVE SURGERY, December 1976, pp. 689–693; August 1972, pp. 107–113; November 1976, pp. 555–560; August 1976, pp. 137–141; January 1980, pp. 30–33; November 1977, pp. 720–724; August 1979, pp. 151–155; July 1980, pp. 71–73; June 1977, pp. 849–850; March 1980, pp. 302–306; and AESTHETIC PLASTIC SURGERY, 1979, 3:339–341; 1978, 2:435–441; and 1978, 2:217–234.

Most of the prior art on the physical structure of breast prostheses, however, is found in the patent literature, particularly the United States patents relating to that subject. The patent literature includes many experimental and non-commercial prostheses as well as ones which have had substantial medical usage. The following patents represent a summary of the most pertinent patent art dealing with breast prostheses.

Cronin U.S. Pat. No. 3,293,663 discloses a breast prosthesis comprising a flexible container filled with a soft gel and a corrugated fabric attached to one side of the container so that tissue can grow through the fabric to anchor the container to the chest wall. This patent is probably the earliest example of a medically acceptable prosthesis which has been commercially produced for many years. However, as noted elsewhere, this prosthesis has been subsequently found to be the focal point of a serious problem, viz. the formation of a tight fibrous capsule which contracts and causes the prosthesis to become hard and painful.

Hartley U.S. Pat. No. 3,934,274 discloses a deflatable breast prosthesis comprising a pair of bags or sacs, one inside the other, filled with liquid. The outer bag is provided with a flap valve through which fluid can be added or removed to adjust the amount of fill. This patent illustrates an attempt to design a prosthesis which could overcome the problem of capsular contracture. However, this prosthesis has been used only to a limited extent and the procedure for softening the prosthesis by removal of fluid through the flap valve has not proved to be technically successful and has been largely abandoned.

A number of U.S. patents disclose various proposed breast prostheses which do not appear to have had general acceptance in the medical literature. These patents may possibly represent experimental devices which have not been accepted for commercial development and usage by the manufacturers of such equipment.

A series of patents to Pangman, starting prior to the Cronin patent, disclose some designs for breast prostheses which do not seem to be in current use. Pangman U.S. Pat. No. 2,842,775 discloses a surgically implantable breast prosthesis for use in surgical reconstruction having an outer layer of sponge material and an inner sac filled with a fluid. Pangman U.S. Pat. No. 3,366,975 discloses a breast prosthesis with a core of plastic foam surrounded by a membrane impervious to fluids and, in turn, covered by a porous layer to which human tissue can adhere. Pangman U.S. Pat. No. 3,559,214 discloses a breast prosthesis for surgical implantation which is hollow and filled with a soft fluid gel but is subdivided into a plurality of compartments. Pangman U.S. Pat. No. 3,683,424 discloses a breast prosthesis for surgical implantation which has an elastic sac containing a foam core and a liquid in the pores thereof and having a tube for adjusting the extent of fill of the implant.

Several U.S. patents disclose various prostheses having fluid or plastic fillers and, in some cases, having means for adjusting the size or extent of fill. These devices do not appear to be available from any commercial source and are assumed to be experimental or prototypes, e.g. Boone U.S. Pat. Nos. 3,600,718; Mohl et al 3,663,968; Perras et al 3,665,520; Perras 3,681,787; McGhan et al 3,852,832; Koneke et al 3,852,833; Lynch 3,883,902; Sanders et al 3,919,724; and Lynch 3,986,213.

Cresswall U.S. Pat. No. 4,035,850 discloses a method and apparatus for insertion of a soft prosthesis through an incision into a human body.

In considering the prior art on breast prostheses, it is necessary to keep in mind the difference between surgically implanted prostheses and external prosthetic devices. The patent literature has numerous examples of external devices which have little or no relevance to surgically implanted prostheses, e.g. Bernhardt U.S. Pat. Nos. 2,542,619; Kausch 2,543,499; Freedman 2,636,182; and Mann 3,619,819.

SUMMARY OF THE INVENTION

One of the objects of this invention is to provide a surgical procedure utilizing a new and improved surgically implanted prosthesis for augmentation or reconstruction of the human female breast which avoids tightness and contracture of the fibrous capsule formed around such implanted prostheses after surgical implantation.

Another object of the invention is to provide a new and improved surgically implanted prosthesis for augmentation or reconstruction of a human female breast including means for effecting encapsulation of the prosthesis only at some distance from the surface of the prosthesis and without contractive pressure thereon.

Another object of the invention is to provide a new and improved prosthesis for surgical implantation in the female human breast for breast reconstruction or augmentation which includes a permanent core prosthesis of selected shape and formed of a non-absorbable material and an outer covering or coating which is temporary and is formed of a material which is absorbable under conditions of use and having an outer surface spaced at a selected and controlled distance from the core.

Still another object of the invention is to provide a new and improved prosthesis for surgical implantation in the female human breast for breast reconstruction or augmentation which includes a core prosthesis of selected shape and formed of a non-absorbable material and an outer covering formed of an absorbable material having an outer surface spaced at a selected and controlled distance from the core.

Still another object of the invention is to provide a new and improved prosthesis for surgical implantation in the female human breast for breast reconstruction or augmentation which includes a core prosthesis of selected shape and formed of a non-absorbable material and an outer sac formed of a material which is absorbable under conditions of use.

Yet another object of the invention is to provide a new and improved prosthesis for surgical implantation in the female human breast for breast reconstruction or augmentation which includes a core prosthesis of selected shape enclosed in a non-absorbable material, an outer sac formed of a material which is absorbable under conditions of use and an inert filler material filling the space within the outer sac and around the core.

Other objects of the invention will become apparent from time to time throughout the specification and claims as hereinafter related.

These and other objectives of the invention are achieved by the novel breast prosthesis which consists of an inner permanent core comprising a container or sac of a flexible, non-absorbable material filled with a fluid or malleable filler material, an outer temporary container, sac, cover or coating of a flexible material which is absorbable or can be rendered absorbable under conditions of use, and an inert filler material, preferably an absorbable liquid, filling the space between the inner and outer containers. The inner core container is preferably of silicone rubber film and is filled with a silicone gel. Other fillers such as inert particulate material or sponge material could be used. The inner core can also be a double lumen prosthesis of the type presently in use with a valve in the outer lumen. Or the inner core can be a single lumen inflatable type also with a valve to adjust the amount of fill. The outer container is of a material which is absorbable, e.g. by dissolution, phagocytosis, hydrolysis, etc., or which can be rendered absorbable under conditions of use. Preferred materials for the outer container are ones which are presently in use in surgical sutures. These and other suitable materials include films, sheets or coatings or reconstituted collagen, polylactic acid, polyglycolic acid, polyglactin 910, polyesters, reconstituted vegetable protein, amylose, amylose derivatives, cellulose derivatives, etc. The liquid filler may be saline solution or the like.

BRIEF DESCRIPTION OF THE DRAWINGS

FIG. 5A is a fragmentary view in section similar to FIG. 5 showing an alternate embodiment in which the outer lumen of the prosthesis does not overlap the back wall of the inner core or permanent component of the prosthesis.

FIG. 6 is a sectional view of a breast similar to that shown in FIG. 1 showing the prosthesis of FIG. 4 at the time of implantation.

FIG. 7 is a sectional view of the prosthesis as implanted in accordance with FIG. 6 after formation of the tissue encapsulation.

FIG. 8 is a sectional view of the prosthesis as shown in FIG. 7 after the outer sac has been absorbed.

FIG. 9 is a sectional view, similar to that shown in FIG. 5, of another embodiment of the breast prosthesis of this invention.

FIG. 10 is a sectional view, similar to that shown in FIG. 6, of still another embodiment of the breast prosthesis of this invention.

FIG. 13 is a sectional view of a prosthesis similar to that of FIG. 11 in which the connection of the absorbable outer component to the core component is as shown in FIG. 5a.

ANALYSIS OF THE PROBLEM

Figure 1:
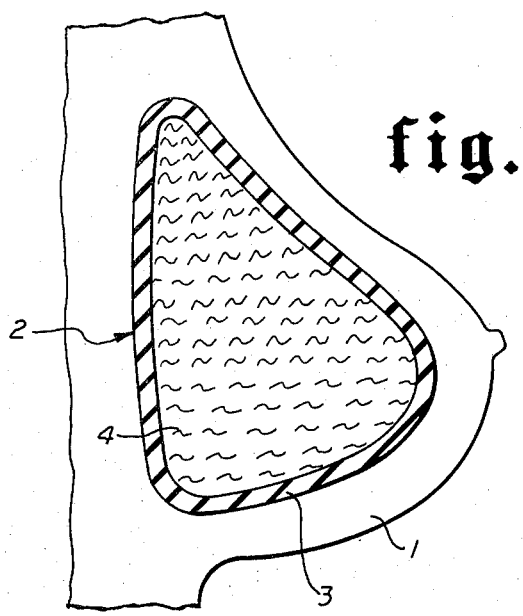
FIG. 1 is a partial section through a female human breast showing a prior art type of prosthesis at or shortly after the time of surgical implantation.

Since the development of the first prosthesis used in breast augmentation and reconstructive surgery, tightness and contracture of the fibrous capsule formed around the prosthesis have been serious problems. Studies show that 35%–40% of patients who undergo breast augmentation develop significant degrees of capsular tightness or contracture which in some cases causes pain and discomfort. Tightness and capsular contracture have caused augmented or reconstructed breasts to have unnatural spherical appearance and to feel hard and undesirable to the touch and palpation. Consequently, the patients as well as surgeons have been less than happy with the results.

Various clinical and laboratory research has been conducted over the last 10-15 years trying to find a solution to the problem. Although significant improvements have been accomplished in the quality of the prosthesis itself, the problem of capsular contraction has not changed appreciably. Several techniques and methods and newer prostheses have been designed and used in an attempt to improve and mitigate the problem of capsular contracture. These techniques have been generally unsuccessful and have been either completely abandoned or used with less enthusiasm. The problem continues to the present day, see any of the recent publications listed above. One of the attempts to solve this problem involved the use of double lumen prostheses which were introduced on the assumption that if capsular contracture occurred the resulting compression on the prosthesis could be relieved by reducing the amount of fluid in the outer lumen. Reducing the fluid was designed to be done by means of a percutaneous hypodermic needle through a valve in the implanted prosthesis. Clinical experience, however, has shown that this procedure is not practical and it has been largely abandoned. It should be noted, that even if this procedure could be used, it would cause the outer sac or bag to wrinkle and create an undesirable appearance for the augmented or reconstructed breast.

Another approach to the problem of capsular contracture has been the use of steroids either by direct instillation in the pocket for the implanted prosthesis or by adding such steroids to the fluid in the outer lumen of an inflatable implanted prosthesis. It was thought that the steroids would gradually pass through the wall of the outer lumen into the surrounding tissues and would suppress the formation of fibrous tissue and consequently make tightness of the encapsulation less likely to happen. It should be noted, however, that there is a substantial difference of medical opinion as to whether steroids have any such effect at all. Also, a major problem with the use of steroids for this purpose is atrophy and depigmentation of the skin. It is seen therefor that there is a great deal of controversy surrounding the use of steroids and serious question as to their utility for this purpose.

Up to this date, the only available way to remedy the capsular contracture has been by surgery. The operation, which is called surgical capsulotomy and capsulectomy, amounts to incising and removing the contracted capsule and implant and inserting either the same or another implant. This operation, of course, may have the same fate as the original one and the same problem of capsular contracture may come about all over again.

Figure 2:
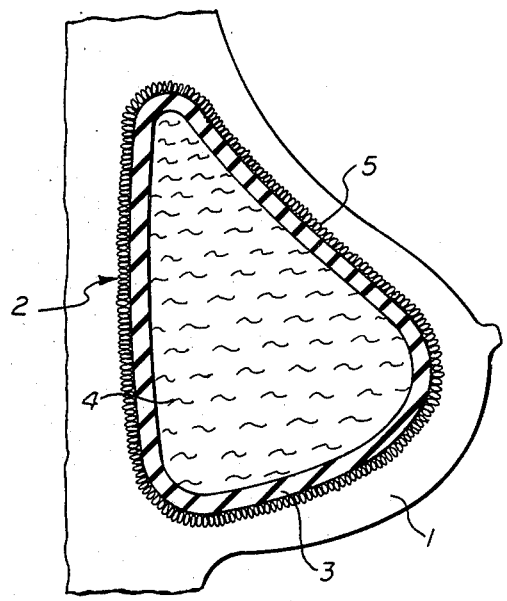
FIG. 2 is a sectional view of the surgical implantation shown in FIG. 1 at a later time after initial formation of a tissue encapsulation.

The problem of capsular contracture can be understood more clearly by reference to FIGS. 1 and 2 of the drawings. In FIG. 1, there is shown a detail view in partial section of a human female breast 1 which has a typical prior-art-type breast prosthesis 2 implanted therein. The prosthesis 2 is preferably a flexible container or sac 3 of a suitable thin walled or film material such as silicone rubber enclosing a core of a soft or fluid or malleable material. Core 4 is preferably of a silicone gel or other suitable material which provides for malleability or plasticity and yet is not unduly soft.

Figure 3:
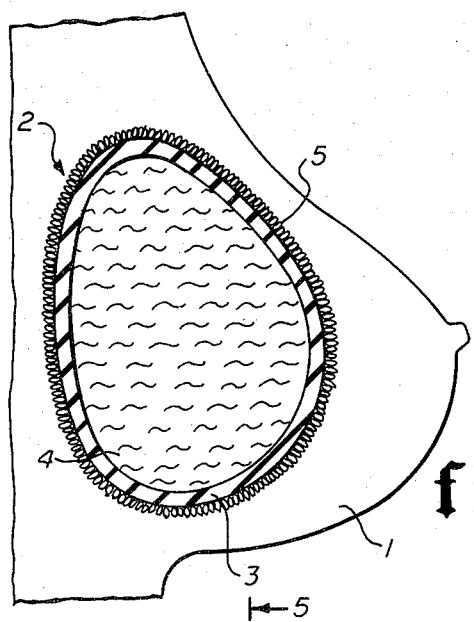
FIG. 3 is a sectional view similar to that shown in FIG. 2 illustrating the condition of the prosthesis after full formation and contracture of the tissue encapsulation.

When a foreign body is implanted in human or animal tissues, the tissues form a fibrous capsule around the foreign body to protect the surrounding tissues. The encapsulation is a defensive mechanism and is somewhat similar to the formation of scar tissue in the healing of a wound or surgical incision. In FIG. 2 of the drawings, the condition of the implanted prosthesis 2 is seen after a period of time when prosthesis 2 has first become encapsulated. The encapsulation is indicated at 5 and represents a fibrous tissue capsule as shown schematically in FIG. 2. Fibrous tissue capsule 5 completely encloses the implanted prosthesis 2 and contracts around prosthesis 2 to cause the prosthesis to be compressed tightly. The contracture of capsule 5 around prosthesis 2 results in the prosthesis developing a feel of being very hard and rigid, and ultimately assumes a nearly spherical shape as illustrated in FIG. 3. The formation of this hard, encapsulated prosthesis is a serious condition both from medical and esthetic viewpoints. It is this condition which has been discussed above and which the prior art techniques have failed to cure.

The problem of capsular contracture is very complex. To find a solution to this problem, a number of physiological and physiopathological facts have been considered.

It is well known that the formation of fibrous connective tissue as a capsule around an implant or around any foreign body is a natural phenomenon. Such a capsule will form regardless of the physical or chemical structure of the foreign body. The normal tissues surrounding the foreign body or implant are reactive toward the intruder and will lay down fibrous tissues which form the capsule. To date, there has been no way to prevent the formation of the fibrous capsule around implants or prostheses or other foreign bodies.

A fibrous capsule always forms around implants or prostheses or foreign bodies in an intimate fashion conforming to their respective shapes and curvatures. The capsule tends to contract tightly around the foreign body being encapsulated. The intimacy of fibrous tissue formation around a foreign body, which by existing techniques is inevitable, is the key factor in the formation of a tightly contracted fibrous capsule. Once the capsule has formed, it is permanent. That is, it will not dissolve or disintegrate by itself or by the enzymes or natural fluids of the body. Also, there is no physical or chemical agent presently available that can be used to alleviate the tightness of the capsule.

After careful consideration of the factors discussed above relating to the nature of the process of formation of the fibrous capsule it was concluded that the only factor in the encapsulation process which can be altered is in the relationship of the capsule to the implanted prosthesis. It was concluded that alteration of the position of the fibrous capsule realtive to the implanted prosthesis would prevent the formation of a tightly contracted capsule.

This invention, therefor, represents a newly designed technique, utilizing a prosthesis of novel construction, whereby the capsule is forced to form at a controlled distance from the implanted prosthesis rather than intimately close to it. This solves the problem completely since there is enough leeway between the implanted prosthesis and the fibrous capsule so that the problem of tightness or contracture is avoided. This is the essence of the invention.

DESCRIPTION OF THE PREFERRED EMBODIMENTS

The invention consists of a two-phase breast prosthesis comprising an inner permanent core of biologically compatible, non-absorbable material surrounded by means to effect capsule formation at a selected and controlled distance therefrom and without contractive pressure thereon after surgical implantation.

The first phase or outer segment is temporary and consists of a flexible walled container or bag of a material which is absorbable or can be rendered absorbable under conditions of use. The second phase or inner segment is permanent and consists of a core which is smaller than and contained in the outer bag or container. The inner core is preferably a smaller container or bag which is made of a non-absorable material, such as a silicone rubber film, and contains a suitable filler, such as a normal saline solution or silicone gel or any other malleable or plastic or fluid material. The space surrounding the core inside the outer bag or container is preferably filled with a saline solution. The distance between the outer container and the inner core can be exactly designed at a controlled measurement and is effective to cause the formation of the fibrous capsule at the same distance from the permanent implanted prosthesis.

MATERIALS OF CONSTRUCTION

As noted above, the outer container or sac is a film or thin walled material or coating which is absorbable under conditions of use or can be rendered absorbable under conditions of use. An "absorbable material", as that term is used herein, is defined as any material which is biologically acceptable and, under the conditions of use, can be absorbed by the body tissues, i.e. dissolved or disintegrated and removed by the body. This definition includes materials which are recognized in the medical literature as being absorbable; materials which have known or readily determined properties permitting absorption or dissolution by the body; and materials which can be treated at the time of manufacture, or prior to, during, or subsequent to surgical implantation to render them capable of absorption or dissolution or the like.

These materials may be absorbed by phagocytosis, enzymatic decomposition, dissolution, hydrolysis, etc. under conditions existing naturally in the body. Alternatively, materials can be used, which are within this definition of absorbable materials, which are absorbable by reason of chemical or physical treatment at the time of manufacture or prior to, during, or subsequent to surgical implantation. This would include materials which are not themselves absorbable but which are or become absorbable under conditions of use. Thus, regenerated cellulose is not itself absorbable but can be rendered absorbable by treatment with the enzyme cellulase. Similar enzymes, e.g. proteinase, collagenase, amylase, etc., are known which will decompose protein, collagen, and amylose materials. Also, some protein materials degenerate at certain conditions of pH. It is thus apparent that the outer container can be formed of materials which are not themselves absorbable, but which can be treated, as by addition of chemicals or enzymes to the materials or to the fluid inside or surrounding the outer container to render such materials absorbable. Materials which can be rendered absorbable in this or similar manner are considered to be within the above definition of absorbable materials.

The initially preferred materials are ones which have had a long established use in surgery, particularly suture materials including properly processed and sterilized animal gut, collagenous materials, and synthetic suture materials such as polyglycolic acid, polyglactin 910, reconstituted collagen, etc. Synthetic films which may be used include synthetic protein film or sheet material made of reconstituted collagen or reconstituted animal or vegetable protein or the like. Other synthetic absorbable materials which may be used include films of absorbable polyesters, such as condensation polymers of hydroxy-organic acids, e.g. polylactic acid, polyglycolic acid, polyglactin 910, etc., and low molecular weight polyesters of glycols or other polyols and dibasic or polybasic acids, e.g. polyesters of succinic acid (succinic acid polyesters as bioabsorbable materials are described in Coquard et al U.S. Pat. No. 3,883,901).

In addition, films may be used which are of naturally occurring materials or derivatives thereof, which have a very low solubility in water. Suitable films include starch films, amylose films, films of cellulose derivatives, such as methyl cellulose, ethyl cellulose, hydroxyethyl cellulose, carboxymethyl cellulose, etc. In the case of these films of carbohydrates or carboydrate derivatives, it should be noted that the important characteristic required is that the film have only a very slight solubility in water. These materials are nontoxic and the ones that are very slightly soluble in water will be dissolved slowly and removed over a period of time. Similar materials can be used which are not soluble or absorbable but which are rendered soluble or absorbable by incorporation of a suitable chemical or enzyme or by a further chemical or enzymatic or physical treatment.

MECHANISM OF FUNCTION OF INVENTION

When this two-phase prosthesis is implanted, the fibrous capsule will form around the phase one or outer temporary container which is at a distance from the core which represents the phase two or permanent part of the prothesis. Over a period of time, the outer bag or container will be absorbed by the body leaving behind a fibrous capsule which is larger than, and not intimately attached to, the inner core of nonabsorbable implant. The distance between the formed capsule and the permanent prosthesis can be exactly predetermined at the time of construction by positioning the outer absorbable layer at the optimum and desired space from the inner non-absorbable permanent core. This will all be described in more detail in connection with the several specific examples of the improved breast prosthesis which is to be described below.

Figure 4:
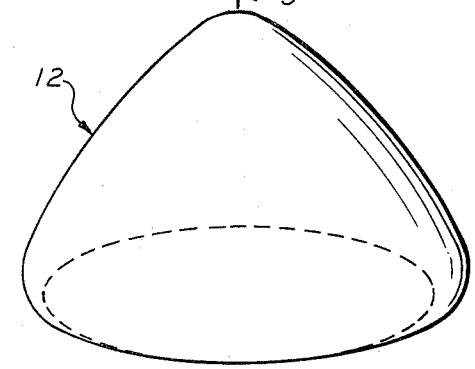
FIG. 4 is an isometric view of a breast prosthesis representing a preferred embodiment of this invention.
Figure 5:
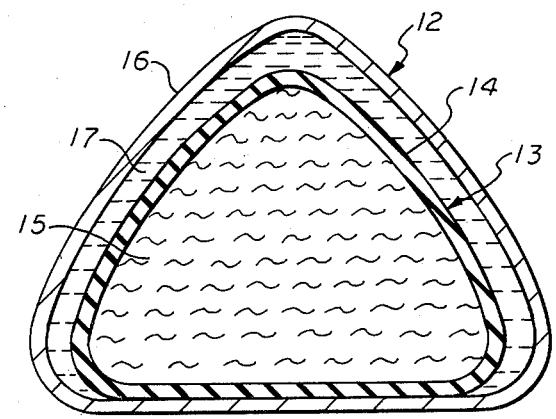
FIG. 5 is a sectional view taken on the line 5—5 of FIG. 4.

In FIG. 4 there is shown an isometric view of an improved, surgically-implantable breast prosthesis 12 which represents a preferred embodiment of the invention. In FIG. 5, breast prosthesis 12 is shown in sectional view along a center line thereof to illustrate the two-phase construction. Breast prosthesis 12 consits of an inner core 13 of biologically acceptable material. Core 13 is preferably a sac or container 14 of a film or thin-walled flexible material, such as silicone rubber and is filled with a liquid or fluid or plastic substance 15. The filler material 15 is preferably a silicone gel or may be a liquid, such as a sterile saline solution. Other malleable or plastic or semifluid materials may be used to fill the sac or container 14 as long as they are sterile, nontoxic and of low density. The core 13 of breast prosthesis 12 is enclosed in an outer sac or container 16 of a thin-walled flexible material or film of a bioabsorbable material. The rear wall of core 13 may be completely covered by outer lumen or sac 16, as seen in FIG. 5, or the outer lumen or sac 16 may be sealed to the edge of the rear wall as indicated at 26 in FIG. 5A. In the embodiment of FIG. 5A, the exposed rear wall of core 13 may be provided with a fabric patch or cover as in the prosthesis of Cronin. The space inside the sac or container 16 and surrounding the core 13 is filled with a suitable biologically acceptable liquid or an absorbable sponge 17.

In the prosthesis, as shown and described in FIGS. 4, 5 and 5A, the outer container or sac 16 is of any suitable absorbable film or thin walled material. Such absorbable material is a material as defined above and should be capable of preparation in a form which can be used in surgical implantation. The mechanism of absorption of the absorbable material depends upon the particular material used. Thus, gut and protein or collagenous films are generally absorbed by phagocytosis. Polyesters and polymers such as polyglycolic acid, polylactic acid, polyglactin 910, etc. are absorbed by hydrolysis and dissolution of the hydrolysis products. Amylose and certain cellulose derivatives are absorbable by slow dissolution. Other films, including cellulose and certain protein films, can be absorbed by enzymatic attack or by physical or chemical decomposition. In the case of materials which are rendered absorbable under conditions of use the enzymes or other chemicals required can be added directly to the film material or can be incorporated into the fluid inside the outer container at the time of manufacture or at a later date (including introduction by hypodermic needle after surgical implantation) or can be instilled in the surgical cavity.

While the outer temporary sac or container 16 is of a nontoxic absorbable material, the inner permanent core 13 is of a biologically acceptable or compatible non-absorbable material and is preferably a sac 14, as previously described, of a biologically acceptable or compatible film or covering or coating material, silicone rubber being a preferred material. The filler material 15 within the core is preferably a gel or semisolid, such as silicone gel or a liquid, such as a saline solution or other similar material. The inner core could also be filled with a powdered or granular material 25 as shown in FIG. 10, all of the other components being the same as shown in FIGS. 4 and 5. In such embodiment, the granular material would have to be a very low density material which is sterile and nontoxic and biologically acceptable. A finely divided cellulose or microspheres of glass or phenolic resin could be used for this purpose. Another embodiment which would function satisfactorily, is shown in FIG. 9, in which the core 13 is of a sponge material 35 which is biologically acceptable and which may be provided with or without the inner sac 14 covering the core. The remaining structure of the prosthesis shown in FIG. 9 is the same as shown and described in FIGS. 4 and 5 and any of the defined materials of construction can be used.

In FIGS. 6 to 8 of the drawings, there is illustrated the results of the implantation of the prosthesis of this invention in a human female breast. In FIG. 6, the prosthesis shown in FIGS. 4 and 5 (or the prosthesis of FIG. 9 or FIG. 10) is shown at the time of original implantation. Prosthesis 12 is shown in section and in the view shown in FIG. 6 is essentially the same section as is seen in FIG. 5. In this view, it is seen that the prosthesis 12 is positioned in place with outer sac 16 surrounding inner core 13 and spaced therefrom by the fluid or saline solution or absorbable sponge 17. The sac or container 16 is of an absorbable material as described above and is in contact with the tissues of the breast in the cavity formed in preparation for installation of the prosthesis. In FIG. 7, there is shown a section of the same breast after the capsule has formed as described for FIG. 2. In this view, it is seen that the tissues forming capsule 5 form on the surface of sac or container 16 which is of an absorbable material. Sac or container 16 is effective to cause the capsule 5 to form at a substantial spacing from inner core 13 as determined by the fluid 17 filling the space around the core 13 inside the outer sac 16. In FIG. 8, the section shown is similar to that in FIG. 7 but represents the condition as it exists several months later. At this time, inner core 13 occupies the same position as shown in FIG. 7. The outer tissue capsule 5 is in substantially the same position as shown in FIG. 7 or may have contracted slightly. The outer sac or container 16, however, has completely disappeared and has been absorbed into the body tissues. The space between capsule 5 and inner core 13 is occupied by fluid material 17 which may be the residue of the solution contained within outer sac or container 16 prior to its biological absorption or may be body fluid. In either case, the outer capsule 5 forms a container or shell which fits loosely around inner core 13 and the prosthesis does not have the tight, hard feel of a prosthesis which is tightly encapsulated as shown in FIG. 3.

Figure 12:
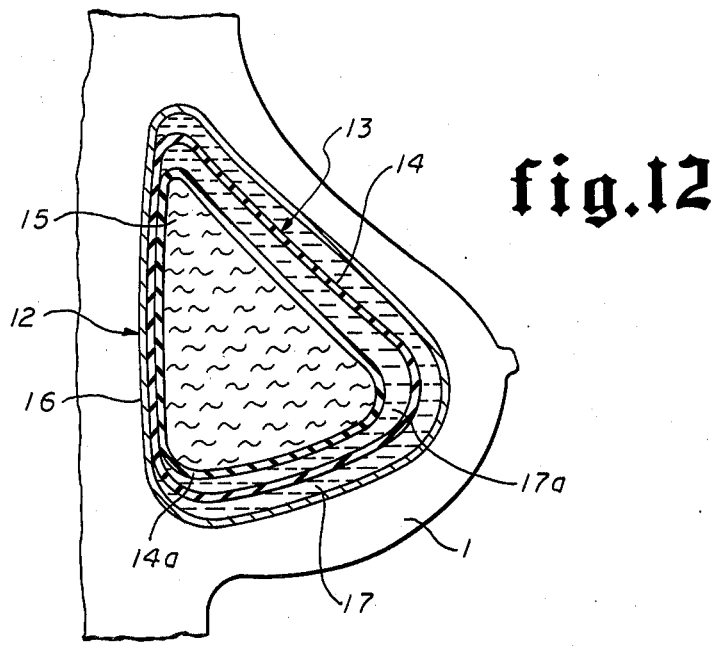
FIG. 12 is a sectional view of a breast with the prosthesis of FIG. 11 implanted therein.
Figure 11:
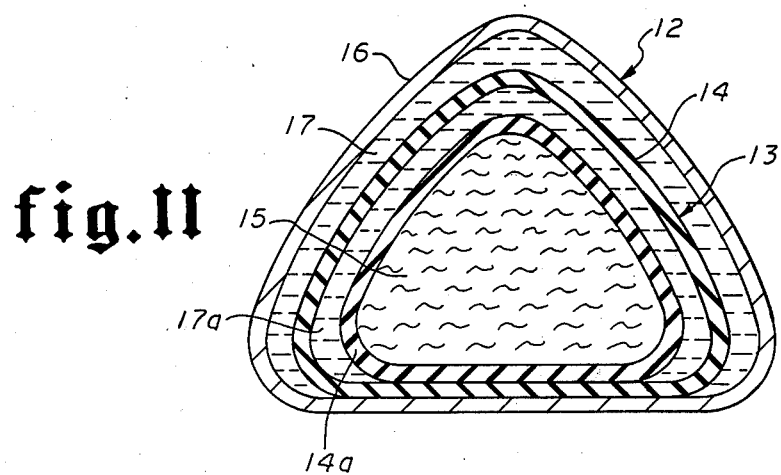
FIG. 11 is a sectional view, similar to that shown in FIG. 5, of an embodiment in which the core or permanent part of the prosthesis is of a double lumen construction.
Figure 13:
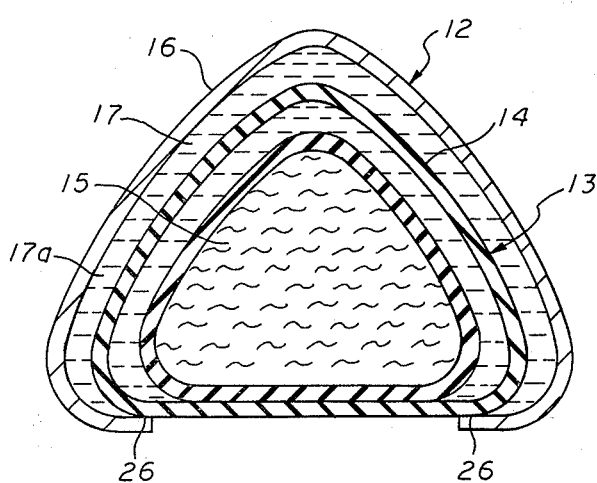

In FIGS. 11–13, there are shown embodiments in which the inner permanent core itself consists of a double lumen construction of a type currently in use. Both lumens 14 and 14a of this structure are made of a non-absorbable material such as silicone rubber. The inner lumen 14a is filled with a liquid such as normal saline or a gel such as silicone gel as indicated at 15. The outer lumen 14 is filled with a compatible solution such as saline as indicated at 17a.

The entire double lumen structure is contained, covered or coated with an absorbable material 16 whose outer surface is at some predetermined distance from the outer surface of the double lumen structure. The outer cover 16 preferably contains a liquid such as normal saline as indicated at 17. In FIG. 13, the same structure is shown except that the outer covering 16 does not cover the back of the core and is sealed thereto as indicated at 26. In FIG. 12, the prosthesis of FIG. 11 or 13 is shown implanted in a female breast.

The advantage of this particular embodiment is that "bleeding" or leaking of silicone gel 15, if this material is used, from the inner lumen 14a will not come in contact with the fibrous capsule. Therefore further stimulation and thickening of the fibrous capsule by the silicone gel molecules will not occur. Whatever leaking of the contents of the inner lumen occurs will be trapped in the outer lumen of the double lumen structure and will not reach the fibrous capsule to cause further thickening.

While this invention has been described fully and completely with special emphasis upon several preferred embodiments it should be understood that within the scope of the appended claims the invention may be practiced otherwise than as specifically described herein.

I claim:

1. A breast prosthesis comprising an inner core of biologically compatible, non-absorbable material, and
    biologically absorbable means surrounding said core for effecting capsule formation at a selected and controlled distance from said core without contractive pressure thereon after surgical implantation.

2. A breast prosthesis according to claim 1 in which said means comprises a flexible wall covering or container surrounding said inner core,
    said biologically absorbable flexible wall covering or container at least at the time of surgical implantation having a biologically compatible liquid in the space between said flexible wall covering or container and said core.

3. A breast prosthesis comprising an inner coherent core of biologically compatible, non-absorbable material and an outer covering of absorbable material having an outer surface spaced from the surface of said core.

4. A breast prosthesis according to claim 2 in which said absorbable material is a material selected from the group consisting of materials which are absorbed by hydrolysis, materials which are absorbed by phagocytosis, materials which are absorbed by enzymatic decomposition and materials which are absorbed by chemical or biological reactions.

5. A breast prosthesis according to claim 3 in which said absorbable material is a material which is formed in situ by reaction of an initially non-absorbable material with added chemicals or enzymes.

6. A breast prosthesis according to claim 5 in which said chemicals or enzymes are added to said initially non-absorbable material at the time of manufacture.

7. A breast prosthesis according to claim 5 in which said chemicals or enzymes are added to said initially non-absorbable material in admixture with fluid introduced inside said outer covering.

8. A breast prosthesis according to claim 7 in which said chemicals or enzymes are added to said fluid after surgical implantation of said prosthesis.

9. A breast prosthesis according to claim 5 in which said chemicals or enzymes are added to said initially non-absorbable material at the time of surgical implantation of said prosthesis.

10. A breast prosthesis according to claim 3 in which said absorbable material is a material which is formed in situ by physical treatment of an initially non-absorbable material to render the same absorbable.

11. A breast prosthesis according to claim 3 in which said outer covering of absorbable material comprises an outer container of a flexible absorbable material spaced from said core, and an inert filler material filling the space between said outer container and said core.

12. A breast prosthesis according to claim 11 in which said outer container comprises a film of a natural or synthetic or semisynthetic absorbable material.

13. A breast prosthesis according to claim 11 in which said outer container comprises a film of a material selected from the group consisting of catgut, chromic gut, reconstituted animal collagen, reconstituted vegetable protein, absorbable carbohydrate polymers, and absorbable synthetic or semisynthetic polymers.

14. A breast prosthesis according to claim 13 in which said film is an absorbable polyester of a dibasic acid.

15. A breast prosthesis according to claim 14 in which said film is an absorbable condensation polymer of a hydroxycarboxylic acid.

16. A breast prosthesis according to claim 15 in which said polymer is polyglycolic acid or polyglactin 910.

17. A breast prosthesis according to claim 11 in which said outer container comprises a film of an absorbable polymer of cellulose or amylose or derivatives thereof.

18. A breast prosthesis according to claim 11 in which said inert filler material is a biologically compatible solution.

19. A breast prosthesis according to claim 11 in which said inner core comprises an inner container of a biologically compatible non-absorbable film enclosing a quantity of fluid material.

20. A breast prosthesis according to claim 19 in which said fluid material in said inner container is a biologically compatible liquid.

21. A breast prosthesis according to claim 19 in which said fluid material in said inner container is a gel material.

22. A breast prosthesis according to claim 19 in which said inner core comprises a container of silicone rubber film enclosing a quantity of silicone gel.

23. A breast prosthesis according to claim 11 in which said inner core comprises a non-absorbable sponge of a biologically compatible material.

24. A breast prosthesis according to claim 11 in which said inner core comprises a sponge enclosed in a biologically compatible, non-absorbable film.

25. A breast prosthesis according to claim 3 in which said outer covering comprises an absorbable sponge.

26. A breast prosthesis according to claim 3 in which said inner core comprises a double lumen prosthesis.

* * * * *